United States Patent [19]
Tanimoto et al.

[11] Patent Number: 6,069,271
[45] Date of Patent: May 30, 2000

[54] PRODUCTION METHOD OF ACRYLIC ACID

[75] Inventors: Michio Tanimoto; Kazuyuki Uekawa, both of Himeji; Tatsuya Kawajiri, Yokohama, all of Japan

[73] Assignee: Nippon Shokubai Co., Ltd., Osaka, Japan

[21] Appl. No.: 09/178,737

[22] Filed: Oct. 27, 1998

[30] Foreign Application Priority Data

Oct. 27, 1997 [JP] Japan .................................. 9-293756

[51] Int. Cl.⁷ .......................... C07C 51/16; C07C 51/25
[52] U.S. Cl. ..................... 562/545; 562/546; 562/547; 422/196; 422/198; 422/201; 422/211
[58] Field of Search ................................. 562/545, 546, 562/547; 422/196, 198, 201, 211

[56] References Cited

U.S. PATENT DOCUMENTS

| | | | |
|---|---|---|---|
| 3,147,084 | 9/1964 | Franzen et al. | 23/288 |
| 4,203,906 | 5/1980 | Takada et al. | 260/346.4 |
| 4,873,368 | 10/1989 | Kadowaki et al. | 562/532 |
| 4,954,650 | 9/1990 | Abe et al. | 562/534 |
| 5,048,601 | 9/1991 | Yamaguchi et al. | 165/140 |
| 5,144,091 | 9/1992 | Martan et al. | 568/479 |

FOREIGN PATENT DOCUMENTS

| | | |
|---|---|---|
| 0383224 | 8/1990 | European Pat. Off. . |
| 2513405 | 10/1976 | Germany . |
| 2001257 | 1/1979 | United Kingdom . |
| 2063861 | 6/1981 | United Kingdom . |

Primary Examiner—Rosalynd Keys
Attorney, Agent, or Firm—Sherman & Shalloway

[57] ABSTRACT

A method for producing acrylic acid from propylene at high efficiency by two-stage catalytic oxidation using a single fixed bed shell-and-tube heat exchanger type reactor is provided. The method comprises dividing the shell space of said reactor into an upper space and lower space with a partition plate, allowing a heating medium to circulate in each of the spaces substantially independently of each other, and carrying out the vapor phase oxidation under specific conditions. Said specific conditions including providing a first stage catalyst layer at lower portion of each of the reaction tubes, a second stage catalyst layer at upper portion thereof and an inert substance layer therebetween, and making void ratio of the inert substance layer 40–99.5%.

10 Claims, 2 Drawing Sheets

PRODUCTION METHOD OF ACRYLIC ACID

This invention relates to a production method of acrylic acid. More specifically, the invention relates to a method for producing acrylic acid from propylene at a high efficiency, using only one fixed bed shell-and-tube heat exchanger-type reactor.

Production of acrylic acid by means of two-stage gaseous catalytic oxidation of propylene has been widely industrially practiced. This method employs a first stage reactor charged with a first stage catalyst suitable for gaseous oxidation of propylene to acrolein and a second stage reactor charged with a second stage catalyst suitable for gaseous oxidation of acrolein to acrylic acid, said method comprising introducing the reaction gas containing mainly acrolein and leaving the first stage reactor into the second stage reactor, and further oxidizing said acrolein in the second stage reactor to produce acrylic acid. Large numbers of catalysts have heretofore been proposed as being suitable for said first stage catalysts and second stage catalysts.

Whereas, should it become possible to practice the same two-stage catalytic oxidation method using only one reactor to produce acrylic acid from propylene at a high efficiency, instead of using the two reactors as above, numbers of reactors and incidental instruments and devices can be markedly reduced, which leads to appreciable reduction in production costs and economical advantages. Such two-stage catalytic oxidation methods to produce acrylic acid from propylene using only one reactor have also been already proposed.

For example, Japanese Patent Publication No. 21966/1979 A, in particular, Example 5 therein, describes a method for producing acrylic acid from propylene by two-stage catalytic oxidation method using only one shell-and-tube heat exchanger type reactor in which each reaction tube is charged with a first stage catalyst and a second stage catalyst. In said method, each reaction tube in the reactor is first charged with a second stage catalyst which forms a second stage catalyst layer, then with Alundum for cooling the reaction gas whereby forming an Alundum layer on said second stage catalyst layer, and finally with a first stage catalyst to form the first stage catalyst layer on the Alundum layer. The two-stage catalytic oxidation is conducted by introducing a starting gas containing propylene into so charged reaction tubes, from the top toward the bottom.

Japanese Patent Publication No. 73674/1995 B1 discloses utilization of a multipipe reactor whose shell space is provided with a partition plate in a method for producing acrylic acid from propylene, but said publication teaches no further particulars.

According to our studies, it was found that there still remained a problem which had to be solved before industrially manufacturing acrylic acid from propylene following the method described in above Patent Publication No. 21966/1979 A. The problem is caused by charging two kinds of oxidation catalysts having different activity mechanisms into one and same reactor. More specifically, the reaction tubes are apt to be plugged with a catalyst component sublimating toward the downstream direction, which originates from the first stage catalyst located upstream side of the reaction gas and is entrained by the reaction gas current (eg., when a molybdenum-containing oxidation catalyst is used as the first stage catalyst, the molybdenum component sublimated from the catalyst), and such high boiling substances as side produced terephthalic acid and the like. The plugging increases pressure drop.

Thus, the present invention aims at solving the problems in conventional methods as above, and providing a method for producing acrylic acid from propylene at a high efficiency, through a two-stage catalytic oxidation reaction using one reactor only.

We have discovered that the above object can be accomplished by a production method of acrylic acid from propylene by two-stage catalytic oxidation method using a fixed bed shell-and-tube heat exchanger type reactor comprising a shell and a large number of reaction tubes provided vertically inside the shell, said shell space being divided into two parts of upper and lower spaces with a partition plate, each of said two spaces being designed to allow circulation of a heating medium independently of each other, and each of the reaction tubes being provided with a first stage catalyst layer and a second stage catalyst layer; said method being characterized in that a layer of an inert substance is provided between the first stage catalyst layer and the second stage catalyst layer in each reaction tube, said inert substance layer having a void ratio within a specific range and furthermore meeting the conditions that it has a length sufficient to cool the reaction gas from the first stage catalyst layer to a temperature suitable for its introduction into the second stage catalyst layer and that it is located at such a position that the catalyst at the upper end of the first stage catalyst layer and the catalyst at the lower end of the second stage catalyst layer are not thermally affected by the partition plate.

Thus, according to the present invention, a production method of acrylic acid is provided, which uses a fixed bed shell-and-tube heat exchanger type reactor comprising a shell and a large number of reaction tubes provided vertically inside the shell, said shell space being divided into two with a partition plate to provide an upper space and a lower space, each of said two spaces being designed to allow circulation of a heating medium substantially independently of each other and in each of the reaction tubes being formed are a first stage catalyst layer of a catalyst suitable for producing mainly acrolein through oxidation of propylene and a second stage catalyst layer of a catalyst suitable for producing acrylic acid through oxidation of acrolein; and which comprises oxidizing propylene at vapor phase with the first stage catalyst to form mainly acrolein, and successively oxidizing the acrolein at vapor phase with the second stage catalyst to produce acrylic acid; the method being characterized in that this vapor phase oxidation is conducted under the following conditions:

(1) at the lower part of each reaction tube, i.e., the part of each reaction tube located within the lower space in the shell, the first stage catalyst layer charged with the first stage catalyst is provided, at the upper part of each reaction tube, i.e., the part of each reaction tube located within the upper space in the shell, the second stage catalyst layer charged with the second stage catalyst is provided, and an inert substance layer charged with an inert substance is provided between the first stage catalyst layer and the second stage catalyst layer;

(2) void ratio of said inert substance layer is between 40 and 99.5%;

(3) said inert substance layer has a length sufficient to cool the reaction gas from the first stage catalyst layer to a temperature suitable for its introduction into the second stage catalyst layer, and is located at such a position that the catalyst at the upper end of the first stage catalyst layer and the catalyst at the lower end of the second stage catalyst layer are substantially free from the thermal influence from the partition plate, and (4) a starting gaseous material containing propylene is introduced from lower parts of the reaction tubes and the reaction gas passes through the reaction tubes as upstreams.

Hereinafter the present invention is specifically explained, referring to the appended drawings.

BRIEF DESCRIPTION OF THE DRAWINGS

FIG. 1 schematically shows, as an example, a known fixed bed shell-and-tube heat exchanger type reactor which is disclosed in aforesaid Japanese Patent Publication No. 21966/1979 A, in which only one reaction tube among many reaction tubes is indicated to represent the rest for convenience. As can be seen from FIG. 1, the shell space in the reactor is divided into the upper space and lower space with a partition plate 11; in the upper part of each reaction tube 12 (i.e., the part of each reaction tube positioned within the upper space of the shell) a first stage catalyst layer 13 is provided; in the lower part of each reaction tube 12 (i.e., the part of each reaction tube positioned within the lower space of the shell) a second stage catalyst layer 14 is provided; and between said first stage catalyst layer 13 and the second stage catalyst layer 14 an Alundum layer 15 is provided. A starting gas 16 is introduced from the top of the reactor and the reaction gas 17 is discharged from the bottom of the reactor.

FIG. 2 schematically shows an example of a fixed bed shell-and-tube heat exchanger type reactor which is useful for the present invention, in which only one reaction tube among the many reaction tubes is shown to conveniently represent the rest of the tubes. As can be seen in FIG. 2, the shell space in said fixed bed shell-and-tube heat exchanger type reactor is divided into the upper space and lower space with a partition plate 21, and a heating medium 28 can be circulated through the upper space and lower space substantially independently of each other. In each of the reaction tubes 22 a first stage catalyst layer 23 filled with a first stage catalyst is provided, on said first stage catalyst layer 23, an inert substance layer 25 filled with an inert substance is provided, and further on this inert substance layer 25, a second stage catalyst layer 24 filled with a second stage catalyst is provided. While said first stage catalyst layer 23, inert substance layer 25 and, likewise, the inert substance layer 25 and the second stage catalyst layer 24, are normally in direct contact, if necessary a member such as a piece of wire net may be placed between these layers. A starting gas 26 is introduced from the bottom part of the reactor, and the reaction gas 27 is discharged from the top of the reactor.

Figure 1:
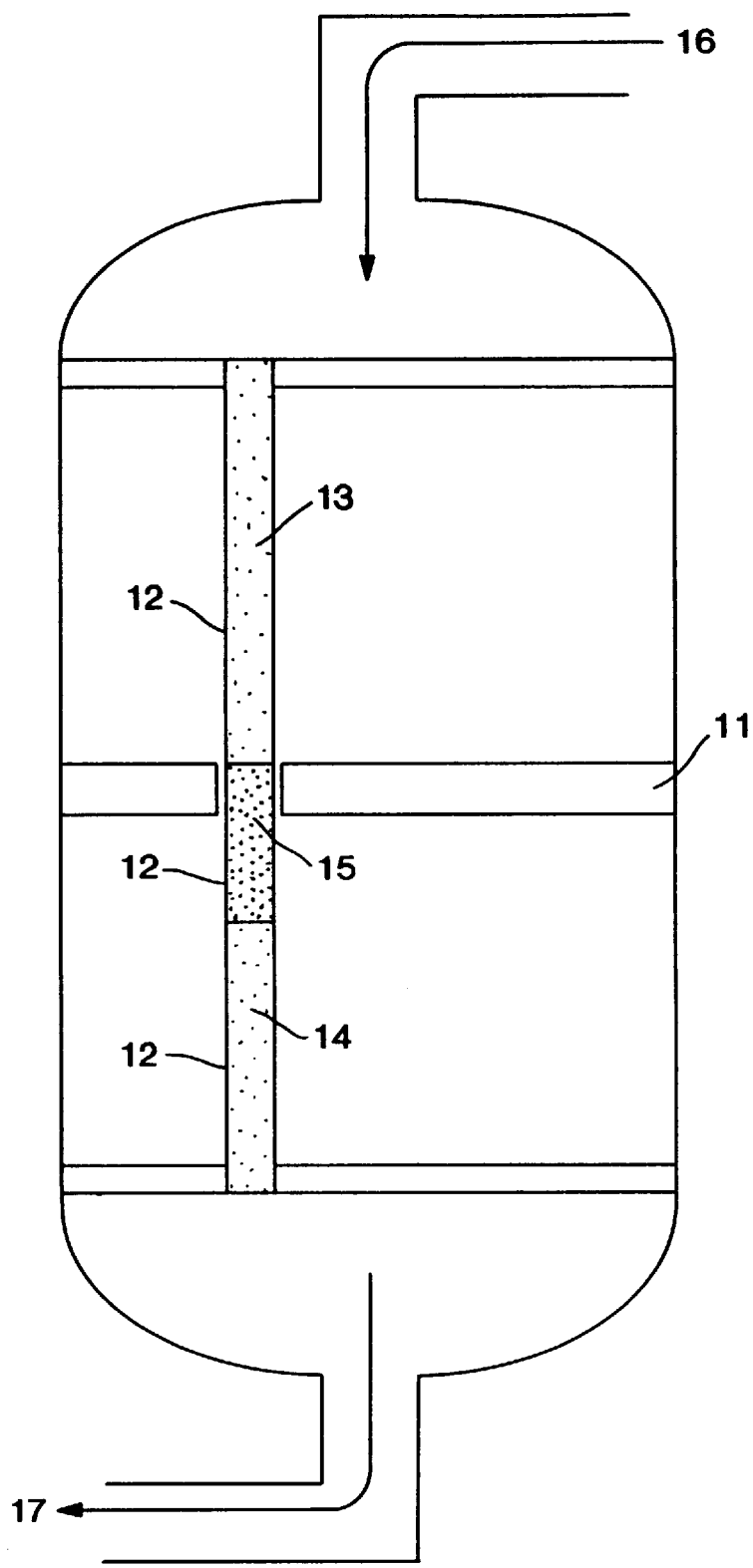
FIG. 1 is a schematic elevation view, of a conventional fixed bed shell-and-tube heat exchanger.
Figure 2:
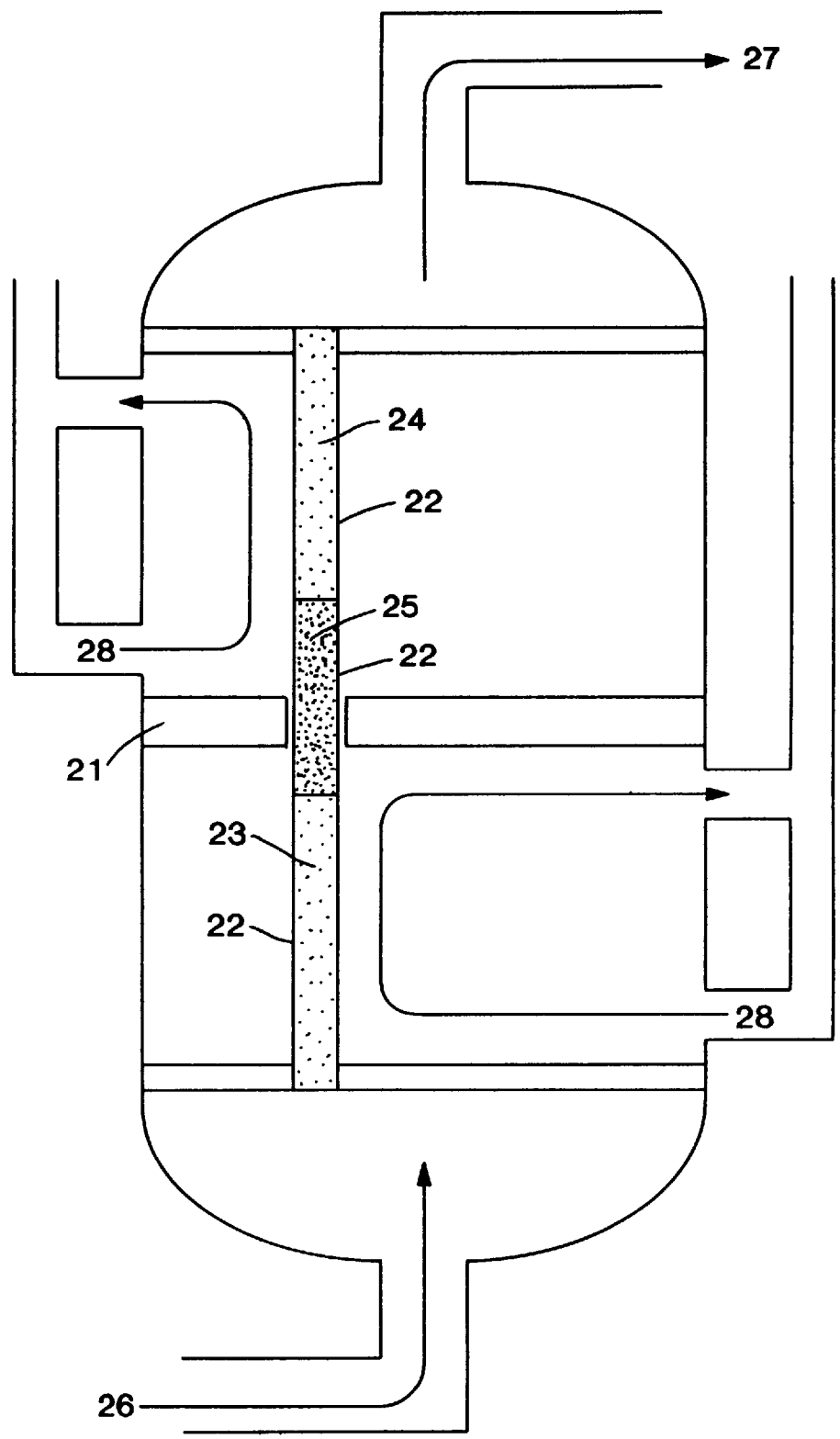
FIG. 2 is a schematic elevation view, of an embodiment of a fixed bed shell-and-tube heat exchanger type reactor useful in carrying out the process of the present invention.

Such construction of a fixed bed shell-and-tube heat exchanger type reactor per se is known (cf. Japanese Patent Publication No. 21966/79 A). In the present invention, the partition plate 21 may be directly fixed on those reaction tubes 22 by welding or like means. Whereas, for preventing thermal distortion from occurring in the partition plate 21 or reaction tubes 22, preferably an adequate gap is provided between the plate 21 and the tubes 22, within a range allowing substantially independent circulation of a heating medium in the upper space and the lower space. Specifically, it is recommendable to provide a gap of about 0.2 to 5 mm between the plate 21 and the tubes 22. Again, while the partition plate 21 may be directly fixed on the inner wall of the reactor by welding or like means, it may be fixed on the inner wall through a cylindrical fixture plate (cf. Japanese Patent Publication No. 73674/1995 B1).

In the fixed bed shell-and-tube heat exchanger type reactor, a heating medium can be circulated through the two spaces substantially independently of each other, which allows easy control of temperatures of the catalyst layers in the reaction tubes, corresponding to the respective spaces (i.e., temperature of the first stage catalyst layer 23 which is charged in the parts of the reaction tubes located within the lower space and that of the second stage catalyst layer 24 which is charged in the parts of the reaction tubes located within the upper space) within each a suitable temperature range for the catalyst to exhibit the respective oxidation function, independently of each other.

Catalysts useful in the first stage according to the invention is subject to no specific limitation but any of oxidation catalysts conventionally used for vapor phase oxidation of starting gases containing propylene to produce mainly acrolein can be used. Similarly, the second stage catalysts are subject to no specific limitation, but any of oxidation catalysts conventionally used for vapor phase oxidation of the reaction gases containing mainly acrolein to produce acrylic acid can be used. Specific examples of those catalysts are as follows.

As the first stage catalysts, for example, those expressed by the formula:

$Mo_a\ Bi_b\ Fe_c\ A_d\ B_e\ C_f\ D_g\ O_x$ (where Mo stands for molybdenum, Bi stands for bismuth, Fe stands for iron, A is at least one element selected from the group consisting of cobalt and nickel, B stands for at least one element selected from the group consisting of alkali metal, alkaline earth metal and thallium, C stands for at least one element selected from the group consisting of tungsten, silicon, aluminium, zirconium and titanium, D stands for at least one element selected from the group consisting of phosphorus, tellurium, antimony, tin, cerium, lead, niobium, manganese, arsenic and zinc, and O stands for oxygen; and a, b, c, d, e, f, g and x express the atomic ratios of Mo, Bi, Fe, A, B, C, D and O, respectively, in which, when a is 12, b is 0.1–10, c is 0.1–20, d is 2–20, e is 0.001–10, f is 0–30, g is 0–4, and x is a numerical value determined by oxidized state of each of the elements) may be named.

As the second stage catalysts, for example, those expressed by the formula, $Mo_a,\ V_b,\ W_c,\ A_d,\ B_e,\ C_f,\ D_g,\ O_x$ (where Mo stands for molybdenum, V stands for vanadium, W stands for tungsten, A stands for at least an element selected from the group consisting of antimony, bismuth, chromium, niobium, phosphorus, lead, zinc and tin, B stands for at least one element selected from the group consisting of copper and iron, C stands for at least an element selected from the group consisting of alkali metal, alkaline earth metal and thallium, D stands for at least an element selected from the group consisting of silicon, aluminium, titanium, zirconium, yttrium, rhodium and cerium, and O stands for oxygen; and a, b, c, d, e, f, g and x express the atomic ratios of Mo, V, W, A, B, C, D and O, respectively, in which, when a is 12, b is 2–14, c is 0–12, d is 0–5, e is 0.01–6, f is 0–5, g is 0–10 and x is a numerical value determined by oxidized state of each of the elements) may be named.

Furthermore, those first stage catalyst and second stage catalyst constituting the first stage catalyst layer and second stage catalyst layer are not necessarily each a single catalyst. For instance, plural first stage catalysts of different activity levels may be charged by the order of their activity levels to form a first stage catalyst layer; or, a part of the catalyst may be diluted with an inert carrier or the like, to vary the activity levels along the length-wise direction of the catalyst layer (direction of the gas flow). The same are applicable also to the second stage catalysts.

Preferred temperature of the first stage catalyst layer 23 normally ranges 300–380° C., and that of the second stage catalyst layer 24 normally ranges 250–350° C. The temperature difference between the first stage and second stage catalyst layers 23 and 24 may range 10–110° C., preferably 30–80° C. It should be noted that the temperature of the first stage catalyst layer 23 and that of the second stage catalyst layer 24 according to the invention substantially correspond to those of the heating medium 28 at the entrances into the shell spaces (i.e., lower space and upper space) corresponding to the respective layers.

Hence, the entrance temperatures of the heating medium 28 into the two shell spaces are determined in correspondence to the respective temperatures of the first stage and second stage catalyst layers 23 and 24, which are set to be within the above specific ranges.

As an inert substance to form the inert substance layer 25 to be provided between the first stage catalyst layer 23 and the second stage catalyst layer 24, any of those which have a void ratio within the range specified in this invention, are substantially inert to the acrolein-containing reaction gas from the first stage catalyst layer, and are capable of cooling said reaction gas to a temperature level suitable for the reaction at the second stage catalyst layer, can be used.

Shape of such inert substance is not critical, so long as it can be filled or accommodated in the reaction tubes. For example, it may be granular, such as of Raschig ring, spherical, cylindrical, ring-formed, or may be in the forms of masses, rods, plates or wire net. Of those, Raschig rings can be conveniently used. When granular or massive inert substances are used, their sizes are not necessarily uniform. Preferably, however, those in which individual particles have a maximum diameter less than the inner diameter of the reaction tube and more than 1/10 of said inner diameter are used. When a rod-shaped inert substance is used, two or more of such particles may be bundled for use. Platy substances may be suitably bent or provided with projections for use.

An inert substance layer according to the invention therefore includes, besides such layers formed by charging granular or massive inert substances, those formed by filling or putting rod-formed or platy inert substances in the reaction tubes. For example, furthermore, for putting bent or folded sheet-formed inert substance, it will be necessary to provide a means suitable for holding the second stage catalyst layer thereon, such as a wire net. Material of the inert substance again is not critical, typical examples including α-alumina, Alundum, murite, carborundum, stainless steel, silicon carbide, steatite, china, porcelain, iron and various ceramics.

While it is not always necessary that an inert substance constituting the inert substance layer, for example, a granular inert substance, is uniformly charged over the all of the inert substance layer, substantially uniform charging over the entire inert substance is preferred for effective cooling of the reaction gas. This statement also applies to inert substances having shapes other than granules.

One of the actions and functions of the inert substance layer is to quench the acrolein-containing reaction gas from the first stage catalyst layer to drop the reaction gas temperature to a range suitable for the oxidation reaction in the second stage catalyst layer. For this purpose, the inert substance layer needs to have a length sufficient to exhibit said action and function. Furthermore, when the first stage and second stage catalysts are in direct contact with the partition plate through the reaction tube walls, their performance is deteriorated under the influence of heat conducted from the plate. The location of the inert substance layer, therefore, must be so determined as to prevent such performance deterioration.

Accordingly, therefore, according to the invention the inert substance layer must have a length sufficient to cool the reaction gas from the first stage catalyst layer to a temperature level suitable for its introduction into the second stage catalyst layer, and must be disposed at such a position as to substantially prevent the thermal influence of the partition plate from affecting the catalyst at the upper end of the first stage catalyst layer (i.e., the catalyst adjacent to the lower end of the inert substance layer) and the catalyst at the lower end of the second stage catalyst layer (i.e., the catalyst adjacent to the upper end of the inert substance layer).

More specifically, it is preferred that the length from the partition plate to the lower end of the inert substance layer is at least 30 mm, and that the length of the inert substance layer is sufficient to cool the reaction gas entering into the second stage catalyst layer from the inert substance layer (i.e., the reaction gas at the entrance of the second stage catalyst layer) to a temperature not higher than the entrance temperature of the heating medium in the upper space by more than 15° C.

Normally the distance between the partition plate and the upper end of the inert substance layer ranges 200–700 mm, preferably 250–600 mm, and that between the partition plate to the lower end of the inert substance layer ranges 30–300 mm, preferably 50–200 mm.

Other actions and functions of the inert substance layer are to prevent an increase in pressure drop during passage of the reaction gas from the first stage reaction zone, which is caused by plugging of the reaction tubes with impurities which are contained in the reaction gas, eg., molybdenum component sublimated from the first stage catalyst and by-produced high boiling substances such as terephthalic acid; and also to prevent these impurities from entering directly into the second stage catalyst layer to deteriorate the latter's catalytic performance. These actions and functions are enhanced when void ratio of the inert substance is decreased. Whereas, excessively low void ratio increases the pressure drop and is undesirable.

Accordingly, according to the present invention, void ratio of the inert substance layer is set to be 40–99.5%, preferably 45–99%. The term, "void ratio" as used herein is defined by the formula below.

$$\text{Void ratio} = \frac{(\text{volume of inert substance layer}) - (\text{true volume of inert substance})}{(\text{volume of inert substance layer})} \times 100 \ (\%)$$

Furthermore, the term, "true volume", as used herein signifies, taking a ring for example, the solid volume not including the central space thereof.

When the void ratio is less than 40%, the pressure drop increases. Whereas, when it is higher than 99.5%, both the function to trap the impurities and that to cool the reaction gas are reduced to produce undesirable results.

According to the present invention, the gaseous starting material containing propylene is introduced from a lower part of each reaction tube and the reaction gas is let pass as an upstream. Whereby it is made possible, as compared to known methods of introducing a propylene-containing starting gas from above the reaction tubes and the reaction gas is passed as a downstream, to reduce contamination of the second stage catalyst with, eg., molybdenum component sublimating from the first stage catalyst and high boiling substances such as terephthalic acid, and the resultant deterioration in performance of the second stage catalyst and increase in pressure drop caused by plugging of the reaction tubes can be decreased.

According to the present invention, the heating medium is preferably let flow upwardly from a lower part, either in the lower space alone of the two shell spaces or in both of the upper and lower spaces. For supplying a heating medium as an upstream, the entrance of the heating medium is provided at a lower part of said space or spaces, and the exit, at a higher part of the space or spaces, and the heating medium is circulated with a heating mediumicirculation device installed outside the reactor. The heating medium is let flow upwardly in at least the lower shell space according to the present invention, because when the heating medium is let flow downwardly in the lower shell space, a space without the heating medium is formed in the area at an upper part of the lower space near the reaction tubes, causing temperature drop at an inside area of the reaction tubes corresponding thereto, which results in occurrence of substantially supercooled parts to give rise to such problems as plugging of the reaction tubes and subsequent increase in pressure drop.

The number of entrances for the heating medium is not critical, which may be one or more than one, and can be optionally determined for individual occasions. Similarly, position(s) of the entrance(s) can be suitably determined, so long as formation of space(s) without the heating medium is prevented and the upstream of the heating medium or a downstream thereof can be secured.

Said "entrance temperature of a heating medium" according to the invention signifies, in respect of the lower shell space, the temperature of the heating medium passing through the entrance located at the lowest end of said space because the flow of heating medium is limited to the upward direction. In respect of the upper space, it signifies the temperature of the heating medium passing through the entrance located at the lowest end of said space when the heating medium forms an upstream, and the entrance located at the highest end when the heating medium forms a downstream.

As above, according to the present invention, a propylene-containing starting gas is introduced from the lower ends of the reaction tubes into each of the first stage catalyst layers to conduct vapor phase oxidation of propylene, and successively the reaction gas containing mainly acrolein is introduced into the second stage catalyst layers in the reaction tubes to conduct vapor phase oxidation of acrolein, whereby the object acrylic acid is produced. In that occasion, composition of the starting gas and the reaction conditions in the first stage and second stage catalyst layers are not subject to critical limitations, but a composition and reaction conditions conventionally employed for this kind of reactions may be adopted.

According to the present invention, acrylic acid can be produced at high efficiency from propylene by two-stage catalytic oxidation method, using only one reactor. Therefore, compared to the conventional methods of conducting the two-stage catalytic oxidation using two reactors, facilities such as piping and heat exchangers become unnecessary to industrial advantage.

Again according to the present invention, such problems as plugging at central parts of reaction tubes and subsequent increase in pressure drop can be solved by provision of afore-described layer of an inert substance. Furthermore, because the reaction gas from the first stage catalyst layer which is apt to induce post-reaction such as autoxidation of acrolein can be sufficiently cooled within a short time down to a temperature range suitable for the reaction in the second stage catalyst layer, the post-reaction can be effectively prevented in the present invention. According to the invention, an yield drop due to excessive oxidation of acrolein can thus be prevented, enabling high yield production of object acrylic acid. Still in addition, the invention so prevents a runaway reaction which takes place under severely excessive oxidation, and safe operation is secured.

According to the invention, furthermore, a propylene-containing starting gas is introduced from lower parts of the reaction tubes and the reaction gas is passed as an upstream, whereby contamination of the second stage catalyst with molybdenum component sublimating from the first stage catalyst layer or with such high-boiling side product as terephthalic acid and the like can be prevented. In consequence, deterioration in performance of the second stage catalyst due to contamination, plugging of the reaction tubes and increase in pressure drop can also be reduced.

Again according to the invention, a heating medium is let flow upwardly in the lower shell space or, in both the lower and upper shell spaces, formation of space(s) without the heating medium can be prevented, which enables substantially uniform temperature control over the whole length of the first stage catalyst layer or, that of the first stage and second stage catalyst layers. Thus, such a problem as a drop in acrylic acid yield due to occurrence of supercooled areas in the reaction tubes can be solved.

Hereinafter the invention shall be more concretely explained, referring to working examples.

EXAMPLE 1

[First stage catalyst]

Into 150 ml of water under heating and agitation, 106.2 g of ammonium molybdate and 32.4 g of ammonium paratungstate were dissolved. Separately, 70.0 g of cobalt nitrate was dissolved in 20 ml of distilled water, 24.3 g of ferric nitrate, in 20 ml of distilled water, 29.2 g of bismuth nitrate, in 30 ml of distilled water which had been made acidic by addition of 6 ml of conc. nitric acid. These three kinds of nitrate solutions were mixed and added dropwise to the first ammonium salt solution. Successively, a solution formed by dissolving 24.4 g of a silica sol containing 20 wt % of silica dioxide and 0.202 g of potassium hydroxide in 15 ml of distilled water was added. Thus obtained suspension was heated under stirring to evaporate water off, and the residue was shaped and calcined at 450° C. for six hours while passing air through the system to prepare a catalyst. The metallic composition of this catalyst was as follows, as expressed by atomic ratios:

$$Co_4Fe_1Bi_1W_2Mo_{10}Si_{1.35}K_{0.06}$$

[Second stage catalyst]

Into 2500 ml of water under heating and stirring, 350 g of ammonium paramolybdate, 106.3 g of ammonium metavanadate and 44.6 g of ammonium paratungstate were dissolved. Separately, 87.8 g of copper nitrate was dissolved in 750 ml of water under heating and stirring, and into said solution 5.9 g of cuprous oxide was added. Thus formed two liquids were mixed and placed in a porcelain vaporizer on a hot water bath. Into the vaporizer further 1000 ml of spherical carrier of 3–5 mm in diameter made of α-alumina was added, and vaporized to driness under stirring, followed by 6 hours' calcination at 400° C. Thus a catalyst on carrier support was obtained. The metallic composition of this catalyst was as follows, as expressed by atomic ratio:

$$Mo_{12}V_{5.5}W_1Cu_{2.7}$$

[Reaction]

A reactor formed of stainless steel reaction tubes of 6,000 mm in total length and 25 mm in inner diameter, and a shell covering the reaction tubes was used. A 50 mm-thick partition plate was provided at a position 3000 mm from the bottom of the shell to divide the shell space into the upper space and lower space and a heating medium was let flow upwardly both in the upper space and the lower space.

Each reaction tube was charged with, from down to up, a first stage catalyst, an inert substance and a second stage catalyst by the order stated, to respective lengths of 2,800 mm, 700 mm and 2,500 mm. Said inert substance was stainless steel Raschig ring of 8 mm in outer diameter, and void ratio of the inert substance layer was 98.5%.

A starting gas composed of 6 vol. % of propylene, 60 vol. % of air and 34 vol. % of steam was introduced from lower ends of the reaction tubes and subjected to the oxidation reactions under the following conditions (flow rate and catalyst layer temperatures).

<Flow rate>

The space velocity (SV) through the first stage catalyst layer was set to be 1500 hr$^{-1}$.

<Catalyst layer temperatures>

Temp. of first stage catalyst layer (entrance temp. of the heating medium into the lower space): 325° C.

Temp. of second stage catalyst layer (entrance temp. of the heating medium into the upper space): 260° C.

Propylene conversions and acrylic acid yields at the initial stage reaction and after 1,000 hours' reaction are shown in Table 1, together with the temperatures of the reaction gas at the entrance of the second stage catalyst layer.

The reaction was stably continued over 4,000 hours without any problem. The pressure drop at the reaction tubes was 6,000 mm (water column) at the initial stage, which was 6,200 mm after 4,000 hours' operation, the increase being only by 200 mm.

EXAMPLE 2

Example 1 was repeated except that stainless steel Raschig ring of 6 mm in outer diameter was used as the inert substance and void ratio of the inert substance layer was made 85%.

The propylene conversions and acrylic acid yields at the initial reaction stage and after 1,000 hours' reaction are shown in Table 1, with the reaction gas temperatures at the entrance into the second stage catalyst layer.

The reaction was stably continued over 4,000 hours without any problem. The pressure drop at the reaction tubes was 6,050 mm (water column) at the initial stage, which was 6,300 mm after 4,000 hours' reaction, the increase being only by 250 mm.

EXAMPLE 3

Example 1 was repeated except that porcelain beads of 8 mm in outer diameter were used as the inert substance and void ratio of the inert substance layer was made 45%.

The propylene conversions and acrylic acid yields at the initial reaction stage and after 1,000 hours' reaction are shown in Table 1, with the reaction gas temperatures at the entrance into the second stage catalyst layer.

The reaction was stably continued over 4,000 hours without any problem. The pressure drop at the reaction tubes was 6,100 mm (water column) at the initial stage, which was 6,700 mm after 4,000 hours' reaction.

EXAMPLE 4

Example 1 was repeated except that the length of the inert substance layer was reduced to 450 mm.

The propylene conversions and acrylic acid yields at the initial reaction stage and after 1,000 hours' reaction are shown in Table 1, with the reaction gas temperatures at the entrance into the second stage catalyst layer.

The reaction was stably continued over 4,000 hours.

EXAMPLE 5

Example 1 was repeated except that the length of the inert substance layer was reduced to 500 mm.

The propylene conversions and acrylic acid yields at the initial reaction stage and after 1,000 hours' reaction are shown in Table 1, with the reaction gas temperatures at the entrance into the second stage catalyst layer.

The reaction was stably continued over 4,000 hours.

COMPARATIVE EXAMPLE 1

Example 1 was repeated except that porcelain beads of 4 mm in outer diameter were used as the inert substance and void ratio of the inert substance layer was made 35%. However, the pressure drop at the reaction tubes of 6200 mm (water column) at the initial reaction stage rose to 8,000 mm after 4000 hours' reaction, and continuation of the reaction over a prolonged period became difficult. After termination of the reaction, inside of the reaction tubes was examined and accumulation of crystalline catalyst component and solid deposit in the inert substance layer was recognized, which was the cause for increase in the pressure drop.

COMPARATIVE EXAMPLE 2

The reaction under the identical conditions with those in Example 1 was attempted, except that the lengths of the first stage catalyst layer, inert substance layer and the second stage reaction layer were changed to 3,000 mm, 200 mm and 2,800 mm, respectively. The reaction, however, was inoperable because of abnormal temperature rise in the second stage catalyst layer which occurred immediately after initiation of the reaction.

COMPARATIVE EXAMPLE 3

The reaction of Example 1 was repeated except that the direction of flows of the heating medium in both the upper space and the lower space was made downward. However, the pressure drop at the reaction tubes which was 6,000 mm (water column) at the initial reaction stage rose to 7,800 mm after 4,000 hours' reaction.

TABLE 1

| | | The Reaction Gas Temperatures at The Entrance into The Second Stage Catalyst Layer (° C.) | Propylene Conversion (mol %) | Acrylic Acid Yield (mol %) |
|---|---|---|---|---|
| Example 1 | Initial reaction stage | 265 | 97.0 | 89.5 |
| | After 1000 hours | 265 | 96.8 | 89.7 |
| Example 2 | Initial reaction stage | 263 | 97.0 | 89.4 |
| | After 1000 hours | 263 | 96.9 | 89.5 |
| Example 3 | Initial reaction stage | 260 | 97.0 | 89.5 |
| | After 1000 hours | 260 | 97.0 | 89.3 |
| Example 4 | Initial reaction stage | 270 | 97.2 | 89.0 |
| | After 1000 hours | 270 | 97.0 | 89.0 |
| Example 5 | Initial reaction stage | 268 | 97.0 | 89.3 |
| | After 1000 hours | 268 | 96.9 | 89.4 |
| Com- | Initial reaction stage | 260 | 97.0 | 89.4 |

TABLE 1-continued

|  |  | The Reaction Gas Temperatures at The Entrance into The Second Stage Catalyst Layer (° C.) | Propylene Conversion (mol %) | Acrylic Acid Yield (mol %) |
|---|---|---|---|---|
| parative Example 1 | After 1000 hours | 260 | 96.9 | 87.0 |
| Comparative Example 2 | Initial reaction stage After 1000 hours | reaction inoperable | | |
| Comparative Example 3 | Initial reaction stage After 1000 hours | 260 260 | 96.8 95.5 | 88.2 86.5 |

We claim:

1. A method for producing acrylic acid in a fixed bed shell-and-tube heat exchanger type reactor for effecting both first stage oxidation of propylene to acrolein and second stage oxidation of acrolein to acrylic acid, said reactor including a shell and a large number of reaction tubes provided vertically inside the shell, said shell space being divided into two with a partition plate to provide an upper space and a lower space, each of said two spaces being designed to allow circulation of a heating medium substantially independently of each other and each of the reaction tubes including a first stage catalyst layer of a catalyst suitable for producing mainly acrolein through oxidation of propylene and a second stage catalyst layer of a catalyst suitable for producing acrylic acid through oxidation of acrolein;

said method comprising oxidizing propylene at vapor phase with the first stage catalyst to form mainly acrolein, and successively oxidizing the acrolein at vapor phase with the second stage catalyst to produce acrylic acid under the following conditions:
(1) at the lower part of each reaction tube, i.e., the part of each reaction tube located within the lower space in the shell, the first stage catalyst layer charged with the first stage catalyst is provided; at the upper part of each reaction tube, i.e., the part of each reaction tube located within the upper space in the shell, the second stage catalyst layer charged with the second stage catalyst is provided; and an inert substance layer charged with an inert substance layer is provided between the first stage catalyst layer and the second stage catalyst layer;
(2) void ratio of said inert substance layer is between 40 and 99.5%;
(3) said inert substance layer has a length sufficient to cool the reaction gas from the first stage catalyst layer to a temperature suitable for its introduction into the second stage catalyst layer, and is located at such a position that the catalyst at the upper end of the first stage catalyst layer and the catalyst at the lower end of the second stage catalyst layer are substantially free from the thermal influence from the partition plate, and
(4) a starting gaseous material containing propylene is introduced from lower parts of the reaction tubes and the reaction gas passes through the reaction tubes as upstreams.

2. The method according to claim 1, which further comprises causing the heating medium to flow upwardly in at least the lower space of the two spaces.

3. The method according to claim 1 or 2, in which the length from the partition plate to the lower end of the inert substance layer is at least 30 mm, and the length of the inert substance layer is sufficient to cool the reaction gas entering into the second stage catalyst layer through the inert substance layer to a temperature not higher than the entrance temperature of the heating medium into the upper space by more than 15° C.

4. In a method for the production of acrylic acid by two stage oxidation of a gas stream containing propylene wherein the two stage oxidation is carried out in a fixed bed shell-and-tube heat exchanger having a large number of reaction tubes arranged vertically inside the shell and a partition plate separating the shell into upper and lower spaces, wherein the reaction tubes in the lower space include a layer of a first stage catalyst effective for oxidizing propylene to acrolein over a first temperature range and wherein the reaction tubes in the upper space include a layer of a second stage catalyst effective for oxidizing acrolein to acrylic acid over a second temperature range, wherein the second temperature range is lower than the first temperature range;

the improvement comprising
providing an inert substance layer having a void ratio in the range of from about 40% to about 99.5% between the first stage catalyst layer and the second stage catalyst layer, said inert substance catalyst layer extending in the region of the partition plate over a length sufficient to cool the reaction gas from the first stage catalyst layer to a temperature within the second temperature range while effectively isolating the upper end of the first stage catalyst layer and the lower end of the second stage catalyst layer from the thermal influence of the partition plate, and,
introducing a starting gas mixture comprising propylene to the lower end of the vertical reaction tubes to thereby flow upwardly through the first stage catalyst layer, inert substance layer and the second stage catalyst layer, whereby impurities present in the reaction gas mixture passing from the upper end of the first stage catalyst layer into the inert substance layer are entrained by said inert substance layer to thereby inhibit pressure drop in the second stage catalyst layer as the reaction gas passes therethrough.

5. The method of claim 4 further comprising circulating a heat exchange medium independently in each of the upper and lower spaces in heat exchange contact with the vertically arranged reaction tubes, wherein the heat exchange medium in at least the upper space is introduced at the lower end thereof and caused to flow to the upper end thereof.

6. The method of claim 5 wherein each of the first stage catalyst layer and the second stage catalyst layer comprise mixed oxides of molybdenum and at least one other metal and wherein the temperature of the first stage catalyst layer is maintained in the range of from 300 to 380° C. and the temperature of the second stage catalyst layer is maintained in the range of from 250 to 350° C. and further wherein the temperature difference between the first and second stage catalyst layers is maintained in the range of from 10 to 110° C.

7. The method according to claim 6 further comprising introducing the circulating heat exchange medium into each of the lower and upper spaces at a temperature corresponding, respectively, to the temperature of the first stage catalyst layer and the second stage catalyst layer.

8. The method according to claim 7 wherein the inert substance layer extends from a distance at least 30 mm below the partition plate upwardly over a length which results in cooling of the reaction gas entering into the second stage catalyst layer to a temperature not more than 15° C. higher than the temperature of the circulating heat exchange medium introduced into the upper space.

9. The method according to claim 1 or claim 4 wherein the inert substance layer comprises granular inert substance.

10. The method according to claim 9 wherein the granular inert substance comprises Raschig rings.

* * * * *